United States Patent [19]
Tobinick

[11] Patent Number: 6,080,147
[45] Date of Patent: Jun. 27, 2000

[54] METHOD OF EMPLOYING A FLASHLAMP FOR REMOVAL OF HAIR, VEINS AND CAPILLARIES

[76] Inventor: Edward L. Tobinick, 100 UCLA Medical Plaza Suite 205, Los Angeles, Calif. 90024-6903

[21] Appl. No.: 09/095,630

[22] Filed: Jun. 10, 1998

[51] Int. Cl.[7] .................................................. A61B 17/52
[52] U.S. Cl. ..................... 606/9; 606/2; 606/10; 606/13
[58] Field of Search ........................... 606/9, 2, 3, 10–14; 607/89, 100

[56] References Cited

U.S. PATENT DOCUMENTS

| | | | |
|---|---|---|---|
| 4,608,978 | 9/1986 | Rohr | 606/9 |
| 5,755,751 | 5/1998 | Eckhouse | 607/88 |
| 5,885,273 | 3/1999 | Eckhouse et al. | 606/9 |
| 5,885,274 | 3/1999 | Fullmer et al. | 606/9 |

*Primary Examiner*—Linda C. M. Dvorak
*Assistant Examiner*—Roy Gibson
*Attorney, Agent, or Firm*—Ezra Sutton

[57] ABSTRACT

A method of removing hair or blood vessels from the skin of a patient using a flashlamp, a sequence control device and an optical delivery system, and includes the steps of controlling the flashlamp to sequentially emit a series of pulses of incoherent light energy, transmitting the series of pulses of incoherent light energy through the optical delivery system to the same spot on the skin containing the hair or blood vessels with the sequential pulses of incoherent light energy transmitted through the optical delivery system from the flashlamp, and pulsing the flashlamp at least two times at a wavelength in the range 550 to 1200 nm, at a power level in the range of 4 to 25 Joules/cm$^2$, each pulse having a duration in the range of ½ to 10 milliseconds, a delay between pulses in the range of 1 to 10 milliseconds, and having a beam diameter on the treatment area in the range of 4 to 50 millimeters.

8 Claims, 5 Drawing Sheets

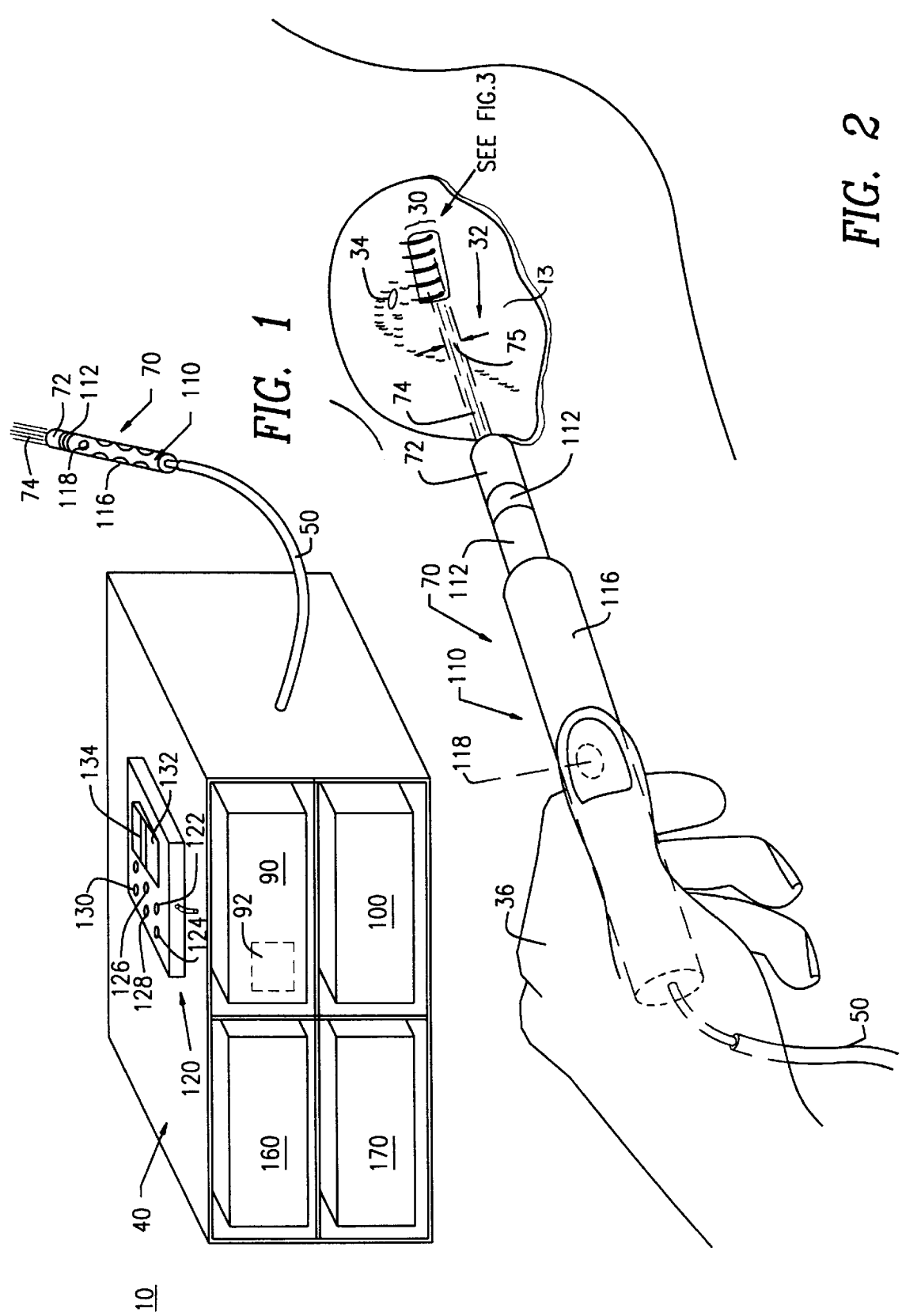

METHOD OF EMPLOYING A FLASHLAMP FOR REMOVAL OF HAIR, VEINS AND CAPILLARIES

FIELD OF THE INVENTION

This invention relates to an improved method of employing a flashlamp for removal of hair, or veins or capillaries, and more particularly, it relates to a flashlamp emitting a series of sequential pulses of incoherent light energy, which are transmitted to the same area of the skin through an optical delivery system.

BACKGROUND OF THE INVENTION

Flashlamps allow the removal of large areas of hair, veins or capillaries on almost any body area, such as on the face, arms, legs, breasts, hands, stomach and the like. Flashlamp treatment provides a low discomfort level to the patient, and hair removal may last for Weeks on a body area. However, the current flashlamp methods used for hair removal sometimes produce unwanted side effects such as burning the skin, changes in skin pigmentation, and permanent scarring.

Pulsed flashlamps emit filtered visible light having wavelengths in the range of 550 nm and above, but have not been effective in providing permanent hair removal.

Current cutaneous flashlamps work by delivering energy in the form of visible light which is absorbed by the cutaneous target, heating the target and thereby causing its destruction. Different skin structures have different colors, different surface to volume configurations, and other factors which cause differential rates of heat loss. All of the hair removal flashlamps work by application of the principal of selective photothermoloysis, i.e. selective destruction due to heat caused by absorption of light. Visible light, which has a varied wavelength, is absorbed by a target which has a complementary specific color for those wavelengths. This flashlamp target is called a chromophore. The usual chromophore for hair removal fiashlamps is melanin, found in high concentration in brown and black hair, and is responsible for the color of hair.

The clinical problem is that melanin is also found in the epidermis, and is responsible for native skin color and tan. Flashlamp energy is therefore also absorbed into the epidermis. The problem of hair removal by flashlamps therefore is to deliver flashlamp energy that heats the hair to a sufficient degree to cause permanent damage and hair loss, yet spare the skin of any damage. Present flashlamp methods are unable to accomplish this.

The use of medical flashlamps to produce permanent hair removal in patients with hair of all colors, and skin of all colors, has, up to this time, been impossible to achieve with current technology. While promising, the currently-used flashlamp methods have all had difficulty in treating patients with dark skin. In addition, even in Caucasian patients, the currently-used flashlamp methods have burned many patients, leading to prolonged changes in skin color and even, in some cases, to permanent scarring. Hair loss, although usually prolonged, has not been permanent for the majority of patients.

Nevertheless, the use of visible light in the range of 550 nm to 900 nm still appears to be an effective way to achieve long-term hair removal. To achieve predictable permanency we need to achieve higher temperatures in the hair without heating the epidermis to the point where it is burned. Current techniques are inadequate to accomplish this.

There remains a need for an improved flashlamp method which will supply a series of short flashlamp energy pulses with short time delays between pulses to heat that hair follicle sufficiently to cause permanent damage to that hair follicle, and yet spare the skin from burning, thus providing a safe and permanent method of hair removal.

A new flashlamp method has been developed that has the following major advantages: 1) increased efficacy, causing greater hair loss and true permanent hair removal; 2) increased safety, with burning of the skin eliminated, so that treatment has no side effects; and 3) it allows the use of flashlamp hair removal for patients with dark skin, thereby greatly increasing the range of people who can be treated with this technology.

DESCRIPTION OF THE PRIOR ART

Flashlamp and laser methods for hair removal have been disclosed in the prior art. For example, U.S. Pat. Nos. 5,630,811 and 5,658,323 to Miller disclose a method and apparatus for dermatology treatments for lesions and hair removal using a modified laser device. The specific target for the laser radiation is the melanin within the hair shaft and within the melanocytes lining of the follicular duct. Pulse width is controlled to provide a direct thermal effect from a single pulse.

U.S. Pat. No. 5,647,866 to Zaias discloses a method of hair depilation through the application of pulsed laser energy having a wavelength readily absorbed by hemoglobin. The process of selective photothermoloysis is used by the laser to focus on a particular region in the epidermis to be irradiated. The pulse duration or time period (30 to 40 nanoseconds) is shorter than the thermal relaxation time for melanin in hair.

U.S. Pat. No. 5,683,380 to Eckhouse discloses a method and apparatus for removing hair (depilation) using a single high intensity pulsed flashlamp which emits a broad spectrum of pulsed incoherent light that is polychromatic. Because of the broad spectrum of wavelengths emitted by the flashlamp, only part of the light energy is absorbed by the hair, making it inefficient for permanent hair removal, although it does provide temporary hair loss.

None of these prior art patents disclose the particular method of the present invention using a flashlamp for safe and permanent hair removal.

Accordingly, it is an object of the present invention to provide an improved flashlamp method which supplies a series of short pulses of flashlamp energy with short delays between the pulses from the flashlamp to beat a hair follicle and hair follicle shaft to cause permanent damage to that hair follicle and shaft, and yet spare the skin from burning, thus providing a safe and permanent method of hair removal.

Another object of the present invention is to provide an improved flashlamp method which sequentially emits a series of pulses of incoherent light energy for permanently removing a plurality of hair follicles, veins or capillaries from the skin area of a patient.

Another object of the present invention is to provide an improved flashlamp method for ease of use by the operator in directing the series of flashlamp pulses at the skin to rapidly remove large areas of hair on almost any body area, such as on the face, hands, arms, legs, breasts, stomach and the like, where such treatment provides a low discomfort level to the patient.

Another object of the present invention is to provide an improved flashlamp method for treatment of other cutaneous conditions (in addition to hair), such as the treatment of leg veins, spider veins, angiomas, lesions, other vascular anomalies and other dermatological conditions effecting the skin of a patient.

Another object of the present invention is to provide an improved flashlamp method for adjusting the number of pulses, the pulse width, the time delay between pulses, and the energy level of each pulse, to customize treatment and the energy delivered to the spot being treated according to skin color, hair color, hair diameter and the anatomic site being treated.

Another object of the present invention is to provide safe and permanent hair removal in a wider range of patients having hairs of all colors and skin of all colors, including patients with dark skin. Generally, the present invention will accommodate all persons having hair which is darker than their skin.

Another object of the present invention is to provide a delay between flashlamp pulses which is much shorter than the thermal relaxation time of the hair being treated, so the hair does not cool off between pulses.

Another object of the present invention is to provide a method wherein the delay between flashlamp pulses is so short that less energy has to be transmitted to the hair to cause permanent hair loss.

SUMMARY OF THE INVENTION

A method of removing hair or blood vessels from the skin of a patient using a flashlamp, a sequence control device and an optical delivery system, which includes the steps of controlling the flashlamp to sequentially emit a series of pulses of incoherent light energy, transmitting the series of pulses of incoherent light energy through the optical delivery system to the same spot on the skin of the patient, irradiating the same spot on the skin containing the hair or blood vessels with the sequential pulses of incoherent light energy transmitted through the optical delivery system from the flashlamp, and pulsing the flashlamp at least two or more times eat a wavelength in the range of 550 to 1200 nm, at a power level in the range of 4 to 25 Joules/cm$^2$, each pulse having a duration in the range of ½ to 10 milliseconds with a preferred range of 1 to 8 ms, a delay between pulses in the range of 1 to 10 milliseconds, and having a beam diameter on the treatment area in the range of 4 to 50 millimeters. The new method requires that a series of relatively low energy flashlamp pulses be delivered in rapid succession with short delays between pulses to exactly the same area of the skin, so that the hair does not have time to dissipate the heat between pulses. Relatively low energy is delivered to the hair germinative apparatus using a series of short pulses from the flashlamp, with the pulses repeated at short intervals so the hair does not have time to dissipate the heat energy between pulses. For most patients, this means five or less low-energy (2 to 15 Joules/cm$^2$) short duration (2 to 6 milliseconds) pulses, separated by short delays of less than 10 milliseconds, each with a large (e.g. 10 millimeters or greater) spot size. The short delay between pulses is shorter than the thermal relaxation time of the hair and skin being treated, so the hair does not cool off between the pulses.

BRIEF DESCRIPTION OF THE DRAWINGS

Further objects, features, and advantages of the present invention will become apparent upon consideration of the detailed description of the presently-preferred embodiments, when taken in conjunction with the accompanying drawings wherein:

FIG. 1 is a perspective view of the flashlamp apparatus of the preferred embodiment of the present invention showing the control box housing having a control panel thereon, the flexible electrical cable, the flashlamp having a handpiece thereon with an operating pulse firing button, shown in an operational mode;

FIG. 2 is an enlarged perspective view of the flashlamp apparatus of the present invention showing the flexible cable and the flashlamp handpiece having a pulse firing button thereon, shown in an operational mode;

DETAILED DESCRIPTION OF THE PREFERRED EMBODIMENT

The flashlamp apparatus 10 and the improved method for permanently removing a plurality of hair follicles 20 from a patient's skin area 14, or for removing blood vessels 28 such as veins and capillaries, are represented in detail by FIGS. 1 and 2 through 5C to 5F.

Figure 5A:
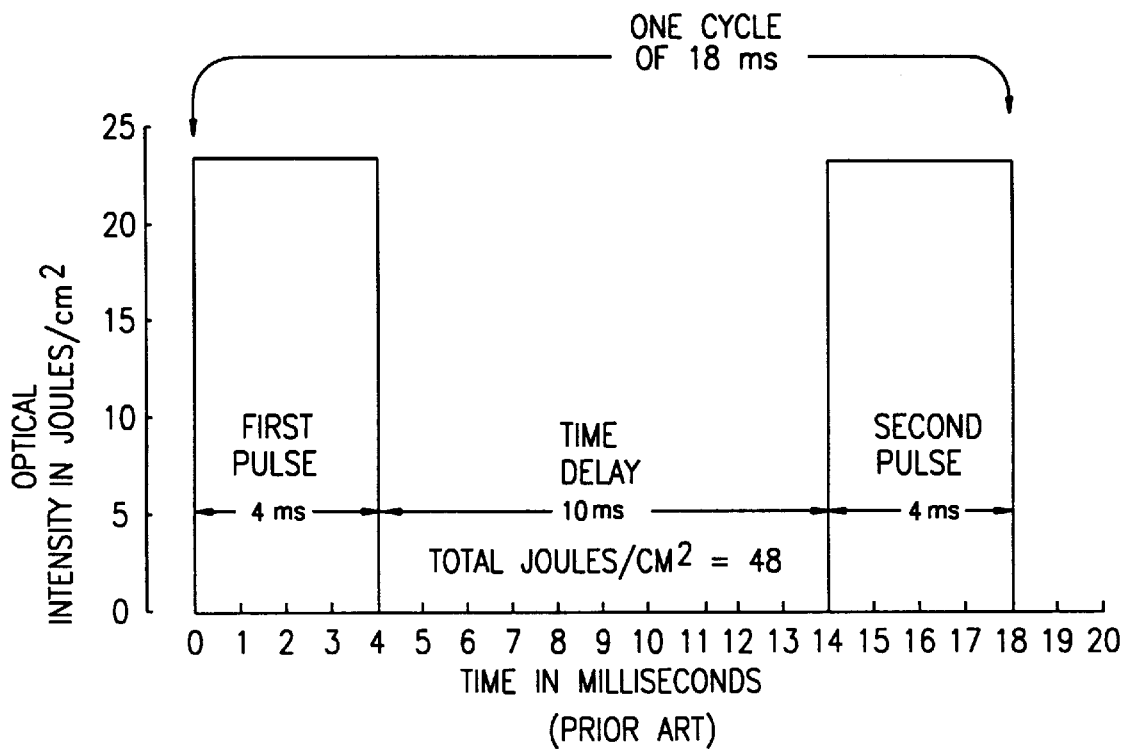
FIG. 5A is a graph showing the lime profile and the optical intensity field performance for the prior art flashlamp used during the hair removal process for fair skin and light hair patient treatments.
Figure 5B:
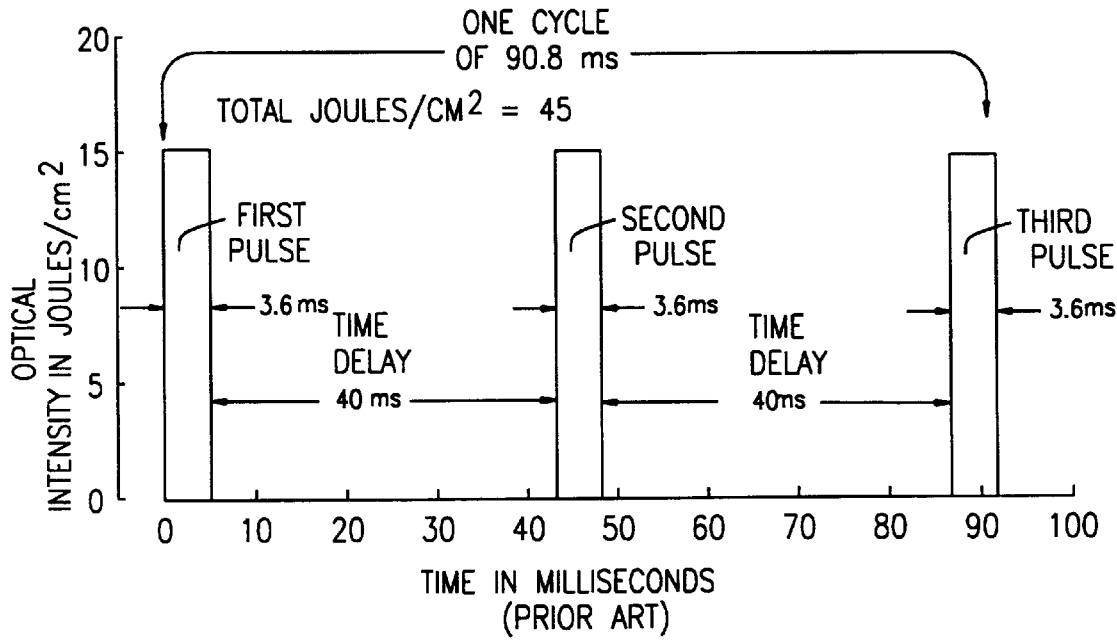
FIG. 5B is a graph showing the time profile and the optical intensity field performance for the prior art flashlamp used during the hair removal process for dark skin and dark hair patient treatments.

FIGS. 5A and 5B show the methods of prior art flashlamps in use with fair skin, light hair patients, and with dark skin, dark hair patients, respectively. FIG. 5A shows two (2) pulses of 4ms each with a time delay of 10 ms for treating fair skin and light hair. In this case, the prior art method uses a pulse delay of 10 ms which is too long and allows the hair to cool too much between pulses. As a result, the hair does not reach a high enough temperature to be destroyed by the second pulse. FIG. 5B shows three (3) pulses of 3.6 ms with two (2) time delays of 40 ms each. Again, in this prior art method, the pulse delays are too long and allow the hair to cool too much between pulses. As a result, the hair does not reach a high enough temperature to be destroyed by this sequence of pulses.

The flashlamp apparatus 10 shown in FIGS. 1 and 2 of the drawings, includes a control box 40 connected to a flashlamp device 70 via electrical cable 50, a computer 90, a capacitor member 100 for discharging the flashlamp light pulses 74, an electrical panel box 160 having electrical circuitry therein, and a power source 170. Electrical cable 50 is connected to a flashlamp handpiece 110 having a pulse firing button 118 thereon. Control box housing 40 includes a flashlamp programmable control panel 120 thereon.

Flashlamp device 70, as shown in FIG. 1, includes a flashlamp projector lens 72 of a specific wavelength for producing an incoherent flashlamp beam 74 having a flashlamp beam diameter 75 of a given width. The electrical cable 50 transmits pulses of coherent light energy (flashlamp beam 74) through the lens 72. Flashlamp device 70 is electrically connected to the computer 90, to the flashlamp programmable control panel 120, and to the electrical panel box 160.

The flashlamp device 70 is adjustable to control the energy level (Joules/cm$^2$), pulse width duration (ms), delay time between pulses (ms), spot size (mm) and wavelength (nm) via the flashlamp programmable control panel 120. The most effective wavelengths for permanent hair removal are in the range of 550 nm to 900 nm when using the flashlamp.

Figure 3:
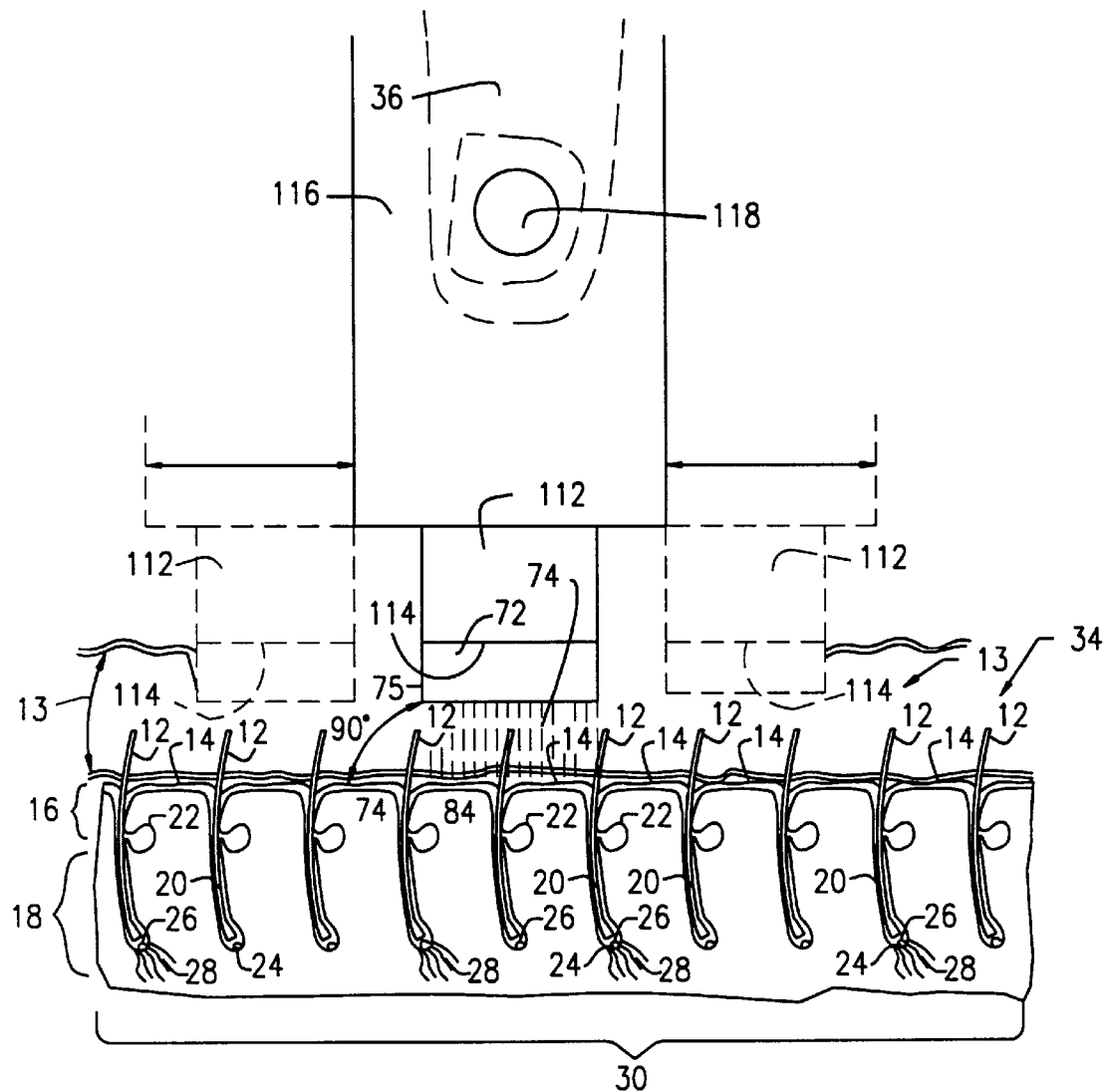
FIG. 3 is a cross-sectional view of a plurality of hair shafts within a region of skin tissue being irradiated with a flashlamp beam from the flashlamp handpiece of the present invention.
Figure 4:
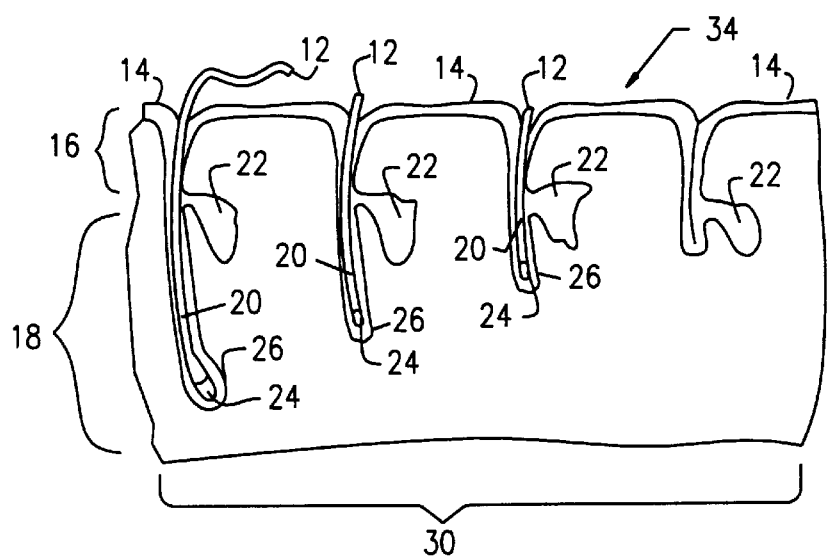
FIG. 4 is a cross-sectional view of a plurality of hair shafts within a region of skin tissue after irradiation by a flashlamp according to the present invention and showing the gradual atrophy of the hair follicle region.

The computer 90 is used for controlling the sequential pulsing of the flashlamp beam 74 from flashlamp device 70, and includes a microcontroller module 92 for controlling the flashlamp 70 to sequentially emit a series of pulses of coherent light energy via capacitor member 100 when the flashlamp operator depresses the pulse firing button 118 on flashlamp handpiece 110. The micro-controller module 92 may be in the form of a microprocessor or an electronic timing device. The series of pulsed flashlamp beams 74 will destroy and permanently remove the plurality of hair follicles 20 from the skin area 14 of a patient, as shown in FIGS. 2 to 4 of the drawings.

The optical delivery system includes the flashlamp handpiece 110 used for delivering and emitting the series of sequential flashlamp pulses 74 from flashlamp device 70, via the micro-controller module 92 of computer 90. Flashlamp handpiece 110 includes a flashlamp dispersal member 112 having a flashlamp portal opening 114 for receiving electrical cable 50 and lens 72 for emitting the flashlamp pulses 74 of flashlamp device 70. Flashlamp handpiece 110 further includes a hand gripping/holding section 116 having a pulse firing button 118 thereon. Pulse firing button 118 is electrically connected to the micro-controller module 92 of computer 90.

The flashlamp programmable control panel 120 is used for controlling the various output functions of energy/power level, in Joules/centimeters$^2$ (J/cm$^2$), the irradiation pulse width duration in milliseconds (ms), the pulse delay in milliseconds (ms), the number of pulses, and the flashlamp beam diameter in millimeters (mm) for the single flashlamp device 70. Control panel 120 includes a plurality of control members 122 to 130 and a visual display screen 132 having a keyboard 134 for programming the aforementioned output functions of energy/power level, pulse width duration, pulse delay, the number of pulses, and flashlamp beam diameter 75. The control panel 120 includes an ON/OFF button 122 for activating and de-activating the flashlamp device 70; a control knob/selector 124 for adjusting the energy/power level of the flashlamp device 70; a control knob/selector 126 for adjusting the irradiation pulse width duration (ms) of flashlamp beam 74 of the flashlamp device 70; a control knob/selector 128 for adjusting the pulse delay of the de-activation time (ms) of flashlamp beam 74 of the flashlamp device 70; and a control knob/selector 130 for adjusting the flashlamp beam diameter 75 of the flashlamp device 70. Control panel 120 is electrically connected to flashlamp device 70 via electrical line 50, as shown in FIG. 1.

METHOD OF THE PRESENT INVENTION;

As depicted in FIG. 3, the plurality of hair shafts 12 project below the epidermis region 16 of skin area 14 and into the dermis region 18. Each hair shaft 12 extends down the follicle 20 and includes a sebaceous gland 22 and which at the anagen stage of the hair cycle further includes a follicular papilla 24 within the hair bulb 26 of hair shaft 12. The follicular papilla 24 is supplied with a plurality of small blood vessels 28 that provide the plurality of growing hair shafts 12 with nourishment. The follicular papilla 24 is an essential structure within the follicle matrix structure 30.

In order to assure destruction of the follicular papilla 24 and permanent hair removal, a sufficient flashlamp energy level is required that destroys the hair but does not burn the skin. In addition, the depth of penetration of the series of flashlamp pulses 74 must be sufficient to cause permanent removal of hair shaft 12 from the epidermis and dermis regions 16 and 18 of the patient's skin area 14.

The flashlamp method of the present invention provides short pulse delays of between 1 ms to 10 ms between pulses, with a preferred pulse delay time of less than 8 ms. The single flashlamp has the capability of sequentially emitting a series of pulses two (2) to six (6) times on the same spot of the patient's skin 14. For example, three (3) pulses may be emitted at 10 Joules/cm$^2$ per pulse each having a pulse width of 2.5 ms and a delay timer between the pulses of 8 ms which allows the delivery of 30 Joules/cm$^2$ to the same spot in 23.5 ms. Various Examples C through F are shown in FIGS. 5C to 5F, respectively, of the drawings.

As shown in FIGS. 2 and 3 of the drawings, the flashlamp operator (not shown) positions the flashlamp dispersal member 112 of the flashlamp handpiece 110 over a selected treatment area, such as the navel area 34 of the stomach 32 of the patient being treated. The flashlamp dispersal member 112 is positioned, as shown in FIG. 3, by the hand 36 of the flashlamp operator such that the series of flashlamp pulses 74 are substantially perpendicular over the selected treatment area, such as a plurality of hair follicles 20 to be removed. Handpiece dispersal member 112 is positioned through a gel compound 13 on the skin 14 at a location (hair that is to be removed) for directing the series of flashlamp pulses 74 to strike the plurality of follicular papilla 24 in order to irradiate them in a proper mode. While the handpiece dispersal member 112 is maintained perpendicular to the skin 14 and on the gel compound 13, it is moved parallel to the plane of the skin and along the surface of the skin area 14 for irradiating successive pluralities of hair follicles 20. The handpiece 110 is then moved vertically to the next horizontal line to repeat the removal procedure. The critical regions of the hair follicle matrix structure 30 include hair follicles 20, sebaceous glands 22 and follicular papillas 24 which are irradiated such that the series of pulsed flashlamp beams 74 can be moved across the skin area 14 or otherwise moved over a large are of skin to be treated.

Application of the series of flashlamp pulses 74 to the plurality of hair follicles 20 and to the plurality of follicular papillas 24 causes selective photothermolysis of the hair germinative apparatus, and more particularly, disruption of the hair follicle matrix structure 30 including vaporization of the deposited melanin, capillary destruction of the papillas 24, as well as vacuolation, edema, gas bubbles and protein denaturation. When the flashlamp pulses 74 applied to the plurality of hair follicles 20 are of sufficient level, these effects will seriously injure each of the hair follicles 20 and papillas 24 being irradiated thereby permanently damaging the hair germ 26 which is responsible for hair regrowth which results in permanent hair removal. The initial flashlamp pulse 74 of flashlamp device 70 heats up the hair follicles 20 and subsequent flashlamp pulses 74 supply further heat energy to vaporize the hair follicles 20, as depicted in FIGS. 3 and 4 of the drawings. This sequential pulsing of flashlamp pulses 74 two (2) to six (6) times per treatment cycle allows the hair temperature of follicles 20 to increase from room temperature of 38° C. to well over 100° C. for the vaporization of the hair follicles 20.

An improved flashlamp method has been provided which, by dividing the flashlamp energy delivery into multiple, individually adjustable pulses, with an adjustable short delay between the pulses, allows it to achieve permanent hair removal without burning the skin on both light and dark skinned patients having either fine or coarse hair. The pulse repetition rate (the delay between pulses) is less than the thermal relaxation time (TRT) of the hair and skin being treated, so that the hair does not have time to dissipate its heat and cool down between pulses. This flashlamp method provides for 1) adjusting the pulse width, the number of pulses, and fluence of the flashlamp; 2) an improved optical delivery system, so that each fired pulse is delivered to precisely the same spot; 3) the operator to precisely define the delay between pulses, and adjust this delay according to clinical variables, such as skin color, hair color, and hair coarseness; and 4) the delivery of these pulses much more rapidly than previous single long pulse flashlamps of the prior art, so that the delay between pulses is less than the TRT of the patient's, hair 12 and skin 14. Treatment may therefore be customized according to skin color, hair color, hair diameter, and the anatomic site being treated, as depicted by Examples C, D, E and F of FIGS. 5C, 5D, 5E and 5F, respectively.

The improved method requires that a series of relatively low energy flashlamp pulses be delivered in rapid succession with short delays between pulses, to exactly the same area of the skin. Relatively low energy is delivered to the hair germinative apparatus using a series of short pulses from the single flashlamp, with the pulses repeated at short intervals so that the hair does not have time to dissipate the heat energy between pulses. For most patients, this means five or less low-energy (2 to 20 Joules/cm$^2$) short duration (2 to 6 milliseconds) pulses, separated by short delays of less than 10 milliseconds, each with a large (e.g., 10 millimeters or greater) spot size. The short delay between pulses is shorter than the thermal relaxation time of the hair being treated, so the hair does not cool off between the pulses.

The clinical circumstances which the flashlamp operator encounters include situations where the characteristics of the flashlamp energy delivered must be dramatically changed in order to deliver enough energy without skin damage to permanently remove the hair. The reason for this is that many variables affect the way flashlamp energy is absorbed. For instance, dark hair absorbs more flashlamp energy than light hair, as does dark skin. Coarse hair retains the heat caused by absorption of flashlamp energy longer than fine hair, and skin cools faster than hair. By taking advantage of these differential rates of heating and cooling one can fashion a series of flashlamp energy pulses that will selectively and permanently remove hair.

For example, an African-American patient with brown skin and coarse, black hair would need to have the energy delivered more slowly with a longer delay between pulses than a Caucasian patient. The delay between pulses is selected to be much less than the TRT of the hair. Successive pulses are then emitted, each one heating the hair more, until permanent destruction of the hair is caused. The skin heats up but not enough to cause damage. As shown by Example F of FIG. 5F, the patient receives three (3) pulses of 2.5 milliseconds each at a energy level of 10 Joules/cm$^2$ each. The time delay between pulses is relatively long (e.g. 8 ms), and the total cycle is 23.5 milliseconds. Thus, 30 Joules/cm$^2$ is delivered safely to a patient in whom 30 Joules/cm$^2$ delivered in a single pulse might burn the skin.

In another example, a patient with olive dark skin would need to have the energy delivered more slowly with a longer delay between pulses than a Caucasian patient. The delay between pulses is selected to be much less than the TRT of the hair. Successive pulses are then emitted, each one heating the hair more, until permanent destruction of the hair is caused. The skin heats up, but not enough to cause damage. As shown by Example E of FIG. 5E, the patient receives three (3) pulses of 2.7 milliseconds, each at a energy level of 11 Joules/cm$^2$ each. The time delay between pulses is relatively long (e.g 6 ms), and the total cycle is 20.1 milliseconds. Thus, 33 Joules/cm$^2$ is delivered safely to a patient in whom 33 Joules/cm$^2$ delivered in a single pulse might burn the skin.

A Caucasian patient with light brown, fine hair, and light, untanned skin requires more energy delivered in order to achieve permanent hair removal. Light, fine hair absorbs little flashlamp energy, but even light skin will absorb some flashlamp energy, which is why pulsed energy delivery, with a delay to allow skin cooling, allows the delivery of more flashlamp energy, safely, to the hair germinative apparatus. In this situation, as shown by Example C of FIG. 5C, the patient receives two (2) pulses of 3.8 milliseconds, each at a energy level of 19 Joules/cm$^2$ each. The time delay between pulses is short (e.g. 1 ms) since light skin cools faster. Thus, 38 Joules/cm$^2$ are thereby delivered safely in two (2) pulses over a 8.6 milliseconds cycle to a patient in whom 38 Jouiles/cm$^2$ delivered in a single pulse might burn the skin.

A Caucasian patient with dark black, fine hair, and light, untanned skin requires more energy delivered in order to achieve permanent hair removal. Dark, fine hair absorbs some flashlamp energy, but even light skin will absorb some flashlamp energy, which is why pulsed energy delivery, with a delay to allow skin cooling, allows the delivery of more flashlamp energy, safely, to the hair germinative apparatus. In this situation, as shown by Example D of FIG. 5D, the patient receives two (2) pulses of 3.8 milliseconds, each at a energy level of 18 Joules/cm$^2$ each. The time delay between pulses is relatively short (e.g. 3 ms) since light skin cools faster. Thus, 36 Joules/cm$^2$ are thereby delivered safely in two (2) pulses over a 10.6 milliseconds cycle to a patient in whom 36 Joules/cm$^2$ delivered in a single pulse might burn the skin.

The actual irradiating of the plurality of hair follicles 20 is accomplished by the flashlamp operator depressing the pulse firing button 118 of flashlamp handpiece 110 which in turn emits a series of flashlamp pulses 74 in a sequenced pulsed cycle over the designated treatment area 30, as shown in FIGS. 2, 3 and 5C to 5F of the drawings. In the foregoing examples, a series of flashlamp pulses 74 of single flashlamp device 70 are sequentially pulsed for an irradiation time of preferably 2 to 6 milliseconds (ms) per pulse (irradiation time can be varied in the range of ½ to 10 milliseconds for each of the flashlamp pulses 74), with a pulse delay duration time between pulses of preferably 1 to 8 milliseconds (pulse delay duration time can be varied in the range of 1 to 10 milliseconds (ms) for each of the flashlamp pulses 74 of flashlamp device 70 being pulsed onto the skin of the patient). A series of sequential irradiation pulses may be emitted two (2) to six (6) times for a complete treatment cycle, as shown in the Examples, which is sufficient to permanently remove the plurality of hair follicles 20 of the patient's skin area 14 being treated.

Figure 5C:
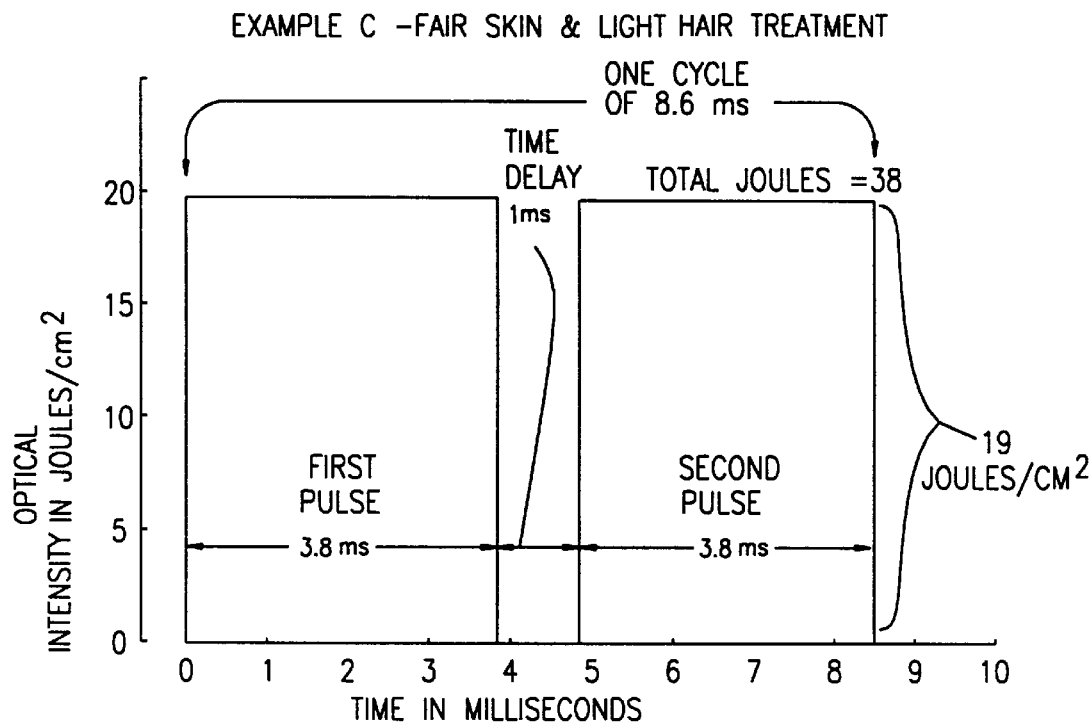
FIG. 5C is a graph showing the time profile and the optical intensity field performance for the sequential pulsing of coherent light energy using a single flashlamp for the hair removal process and treatment of Caucasian patients with fair skin and light hair.
Figure 5D:
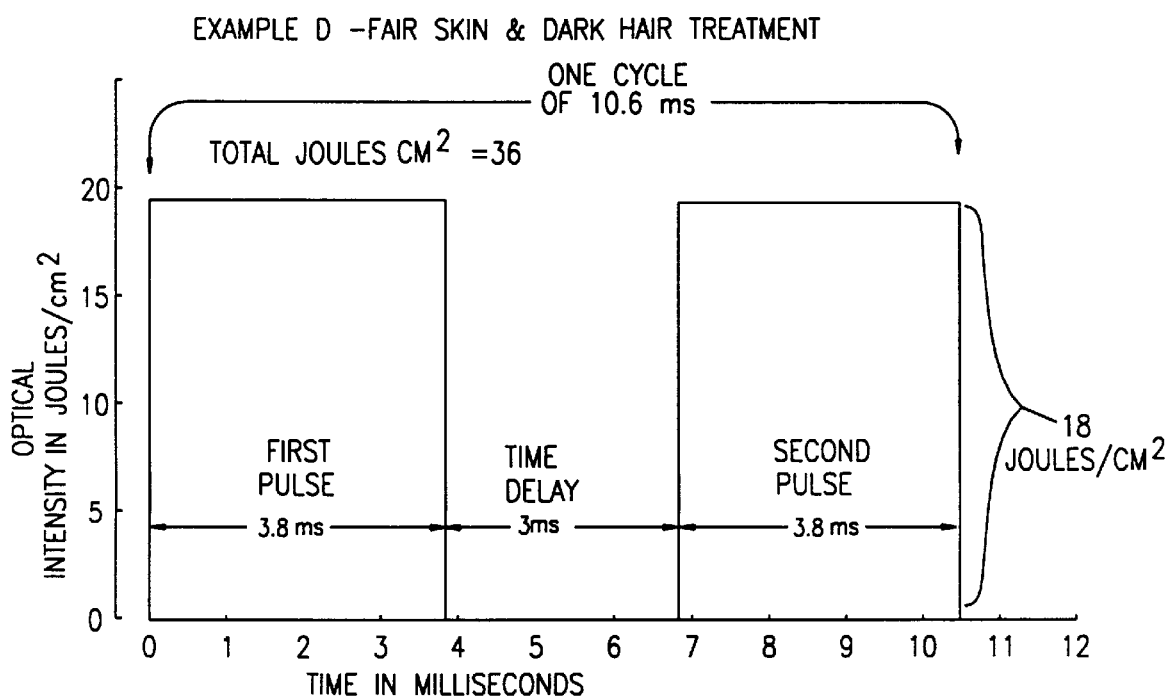
FIG. 5D is a graph showing the time profile and the optical intensity field performance for the sequential pulsing of coherent light energy using a single flashlamp for the hair removal process and treatment of Caucasian patients with fair skin and dark hair.
Figure 5E:
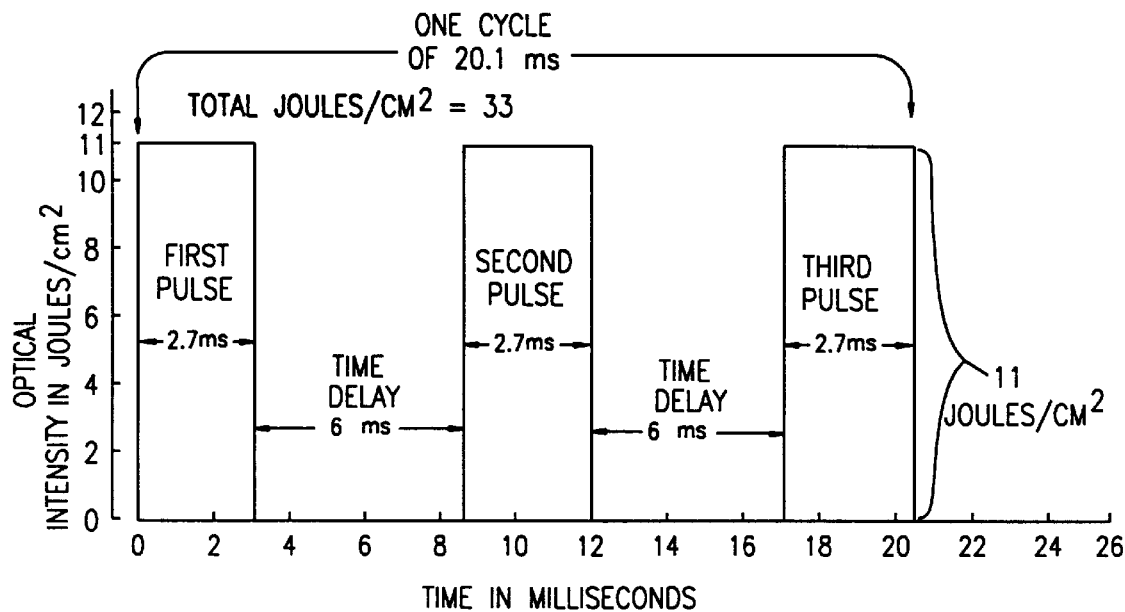
FIG. 5E is a graph showing the time profile and the optical intensity field performance for the sequential pulsing of coherent light energy using a single flashlamp for the hair removal process and treatment of patients with olive skin and dark hair.
Figure 5F:
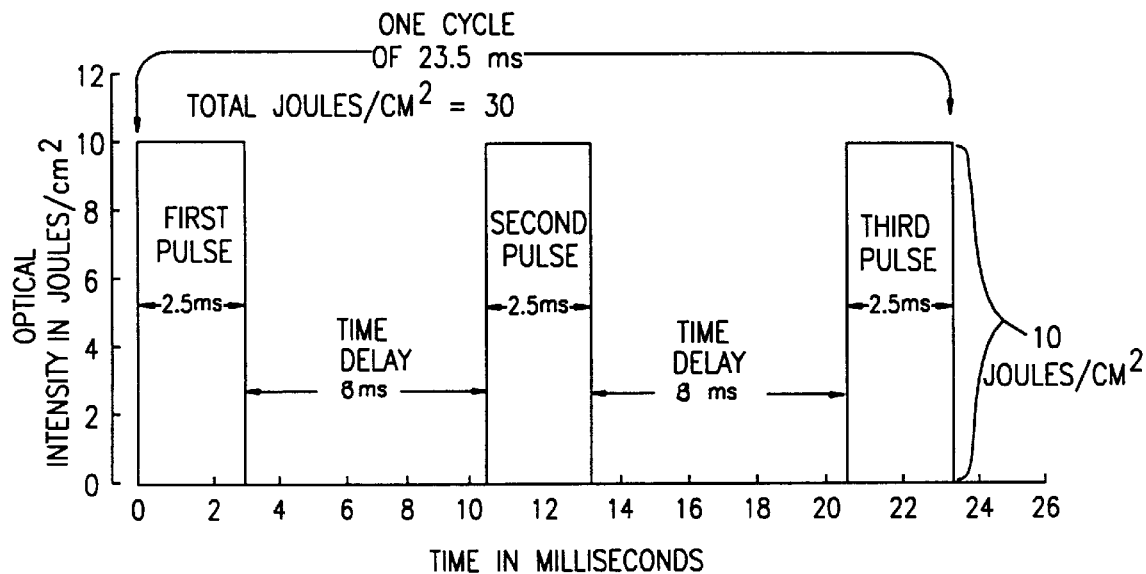
FIG. 5F is a graph showing the time profile and the optical intensity field performance for the sequential pulsing of coherent light energy of a single flashlamp for the hair removal process and treatment of African-American patients with dark skin and dark hair.

In the specific Example C of a two (2) pulse cycle, as shown in detail by FIG. 5C, flashlamp 70 is controlled by sequence control device 90 so that flashlamp 70 emits a 3.8 ms pulse at an energy level of 19 Joules/cm$^2$, then there is a 1ms delay, and then flashlamp 70 emit another sequential 3.8 ms pulse at an energy level of 19 Joules/cm$^2$ to the same spot. This short delay between pulses is enough time to allow the skin being treated to slightly cool the skin 14 so that it can receive the energy (e.g. 38 Joules/cm$^2$) safely without burning the skin and permanently remove the hair in a cycle time of 8.6 milliseconds. In addition, the 38 Joules/cm$^2$ is enough energy to burn the hair follicles over a larger spot size so that a larger area of the patient can be treated in substantially less time. Spot size 75 may be circular or rectangular and a grid pattern may be used for ease of moving handpiece assembly 110 across the patient's skin 14.

Another treatment cycle for permanently removing hair follicles 20 using a flashlamp 70 would have the flashlamp operator pulsing the flashlamp pulses 74 at an energy level of 7.5 Joules/cm$^2$ per pulse with an irradiation pulse duration of 4 ms per pulse for a series of four (4) pulses. The time delay between each of the 4 pulses would be 5 ms so there would be three (3) time delays between the four (4) irradiation pulses. The complete treatment cycle includes pulsed irradiation time (4×4 ms) of 16 ms plus three (3) time delay segments (3×5 ms) of 15 ms for a total treatment cycle time (16 ms+15 ms) of 31 ms at a total energy level of 30 Joules/$^2$ (4 pulses×7.5 Joules/cm$^2$ per pulse). This treatment cycle is sufficient to safely and permanently remove the plurality of hair follicles 20 being treated by flashlamp pulses 74 of the flashlamp apparatus 10.

In another example, the flashlamp operator may want flashlamp device 70 to operate and emit a series of pulses of flahlamp beams 74 sequenitially at different pulse durations of 5 ms, 4 ms, and 3 ms with different delay times of 6 ms and 5 ms between the pulses, at an energy level of 10 Joules/cm$^2$ per pulse, with a flashlamp beam diameter 75 of 10 millimeters. For this specific treatment cycle the operator would program the above data into the programmable control panel 120, as shown in FIG. 5B of the drawings, in the following manner. The flashlamp operator initiates the programming of this specific treatment cycle by turning ON the control panel 120 via ON/OFF button 122. The operator then selects and activates the control knob 124 for adjusting the power level to 10 Joules/cm$^2$ for flashlamp device 70, and then the operator keys in the 10 Joules/cm$^2$ via keyboard 134 for each of the 5 ms, 4 ms and 3 ms pulses and this data is then visually displayed on display screen 132. If the power level for each pulse duration is correct the operator presses the "ENTER" key on keyboard 134 in order to enter the data in control panel 120. Next, the flashlamp operator then selects and activates the control knob 130 for adjusting the flashlamp beam diameter 75 of flashlamp device 70 to be a 10 millimeter diameter.

Then the operator keys in the 10 millimeters for flashlamp beam diameter 75 via keyboard 134 for each of the 5 ms, 4 ms and 3 ms pulses, and this data is then visually displayed on display screen 132. If the flashlamp beam diameter 75 for each pulse duration is correct the operator presses the "ENTER" key on keyboard 134 in order to enter this data in control panel 120. The next step of programming by the flashlamp operator is the selection and activation of the control knob 126 for pulse duration of flashlamp 70, at which time the operator then keys in the aforementioned data/information via keyboard 134 so that the first pulse duration is 5 ms, the second pulse duration is 4 ms and the third pulse duration is 3 ms, and it is then visually displayed on display screen 132. If the series of pulse durations are correct the operator presses the "ENTER" key on keyboard 134 to enter the above data Into the programmable control panel 120. The last step of programming by the flashlamp operator is the selection and activation of the control knob 128 for pulse delay time between irradiation pulses of flahlamp device 70, at which time the operator then keys in the aforementioned information via keyboard 134 so that the first pulse delay time of 6 ms is between the pulses of 5 ms and 4 ms, and the second delay time of 5 ms is between the pulses of 4 ms and 3 ms, and it is then visually displayed on display screen 132 if the series of time delays between pulses are correct, the operator presses the "ENTER" key on keyboard 134 to enter the above information/data in the programmable control panel 120.

Flashlamp apparatus 10 is now ready to fire the series of flashlamp pulses 74 as programmed. Flashlamp operator depresses the pulse firing button 118 over the selected treatment area 34 to start the pulsed treatment cycle. There is a first pulse irradiation time of 5 ms followed by a first time delay of 6 ms, sequentially followed by a second pulse irradiation time of 4 ms followed by a second time delay of 5 ms, and sequentially followed by a third pulse irradiation time of 3 ms. The complete treatment cycle of pulsed irradiation and delay times is thus 23 milliseconds at a total energy level of 30 Joules/cm$^2$ (three (3) pulses at 10 Joules/cm$^2$ per pulse) which is sufficient to permanently remove the plurality of hair follicles 20 of the patient's skin area 14 being treated by flashlamp beams 74 of flashlamp apparatus 10, as shown in FIG. 3 of the drawings.

As shown in FIG. 4, the flashlamp-damaged follicles 20 will gradually recede due to destruction of the follicle matrix structure 30, including disruption of blood flow from the blood vessel capillaries 28 to each of the papillas 24. The hair follicles 20 show gradual atrophy without a blood supply thereby causing permanent hair removal.

Different types of hair and skin pigmentation, different cooling times of the epidermis, and hair follicles of different sizes, as well as the location of body hair to be removed will require different sequences of flashlamp treatment to fit the individual needs of the patient undergoing the therapeutic flashlamp treatment for permanent hair removal. This flashlamp treatment of sequential flashlamp pulses 74 allows the flashlamp operator to individually adjust each of the output functions of energy/power level, pulse width duration, number of pulses, pulse delay and flashlamp beam diameter 75 for the particular patient by using control panel 120 which controls the single flashlamp device 70 of flashlamp apparatus 10 of the present invention

ADVANTAGES OF THE PRESENT INVENTION

Accordingly, an advantage of the present invention is that it provides an improved flashlamp method which supplies a series of short pulses of flashlamp energy with short delays between the pulses from the flashlamp to beat a hair follicle and hair follicle shaft to cause permanent damage to that hair follicle and shaft, and yet spare the skin from burning, thus providing a safe and permanent method of hair removal.

Another advantage of the present invention is that it provides for an improved flashlamp method which sequentially emits a series of pulses of incoherent light energy for permanently removing a plurality of hair follicles, veins or capillaries from the skin area of a patient.

Another advantage of the present invention is that it provides for an improved flashlamp method for ease of use by the operator in directing the series of flashlamp pulses at the skin to rapidly remove large areas of hair on almost any body area, such as on the face, hands, arms, legs, breasts, stomach and the like, where such treatment provides a low discomfort level to the patient.

Another advantage of the present invention is that it provides for an improved flashlamp method for treatment of other cutaneous conditions (in addition to hair), such as the treatment of leg veins, spider veins, angiomas, lesions, other vascular anomalies and other dermatological conditions effecting the skin of a patient.

Another advantage of the present invention is that it provides for an improved flashlamp method for adjusting the number of pulses, pulse width, the time delay between pulses, and the energy level of each pulse, to customize treatment and the energy delivered to the spot being treated according to skin color, hair color, hair diameter and the anatomic site being treated.

Another advantage of the present invention is that it provides safe and permanent hair removal in a wider range of patients having hairs of all colors and skin of all colors, including patients with dark skin. Generally, the present invention will accommodate all persons having hair which is darker than their skin.

Another advantage of the present invention is that it provides a delay between flashlamp pulses which is much shorter than the thermal relaxation time of the hair being treated, so the hair does not cool off between pulses.

Another advantage of the present invention is that it provides a method wherein the delay between flashlamp pulses is so short that less energy has to be transmitted to the hair to cause permanent hair loss.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. A method of removing hair or blood vessels from the skin of a patient using a flashlamp apparatus having a flashlamp, a sequence control device and an optical delivery system, comprising the steps of:

a) controlling said flashlamp to sequentially emit a series of pulses of incoherent light energy, each having a pulse width in the range of ½ ms to 10 ms;

b) transmitting said series of pulses of incoherent light energy through said optical delivery system to the same spot on the skin of the patient;

c) irradiating the same spot on the skin containing the hair or blood vessels with said series of sequential pulses of incoherent light energy transmitted through said optical delivery system from said flashlamp; and d) pulsing said flashlamp at least two times through said optical delivery system at a wavelength in the range of 550 to 1200 nm, at a power level in the range of 4 to 25 Joules/cm$^2$, each pulse having a duration in the range of ½ to 10 milliseconds, a delay between pulses in the range of 1 to 10 milliseconds, and having a beam diameter on the treatment area in the range of 4 to 50 millimeters.

2. A method of removing hair or blood vessels from the skin of a patient using a flashlamp apparatus having a fleshlamp, a sequence control device and an optical delivery system, comprising the steps of:

a) controlling said flashlamp to sequentially emit a series of pulses of incoherent light energy, each having a pulse width in the range of ½ ms to 10 ms;

b) transmitting said series of pulses of incoherent light energy through said optical delivery system to the same spot on the skin of the patient;

c) irradiating the same spot on the skin containing the hair or blood vessels with said series of sequential pulses of incoherent light energy transmitted through said optical delivery system from said flashlamp; and d) pulsing said flashlamp to have a pulse delay between each of said pulses less than the thermal relaxation time (TRT) of the patient's hair in order to remove the patient's hair and in order to avoid burning of the patient's skin, said pulse delay between each of said pulses being less than 10 ms.

3. A method of removing hair in accordance with claim 2, wherein said pulse width has a range of 2 to 6 milliseconds, in duration.

4. A method of removing hair in accordance with claim 2, wherein said delay between pulses has a range of 1 to 8 milliseconds in duration.

5. A method of removing hair in accordance with claim 2, wherein said power level has a range of 4 to 25 Joules/cm$^2$ per pulse.

6. A method of removing hair in accordance with claim 2, wherein said pulsing of said flashlamp includes a beam diameter having a range of 4 to 50 millimeters.

7. A method of removing hair in accordance with claim 2, wherein aid delay between pulses has a range of 2 to 4 milliseconds in duration for a sequence of two pulses.

8. A method of removing hair in accordance with claim 2, wherein said delay between pulses has a range of 3 to 6 milliseconds in duration for a sequence of three pulses.

* * * * *

(12) EX PARTE REEXAMINATION CERTIFICATE (8015th)
United States Patent
Tobinick

(10) Number: US 6,080,147 C1
(45) Certificate Issued: Feb. 8, 2011

(54) METHOD OF EMPLOYING A FLASHLAMP FOR REMOVAL OF HAIR, VEINS AND CAPILLARIES

(76) Inventor: Edward L. Tobinick, 100 UCLA Medical Plaza Suite 205, Los Angeles, CA (US) 90024-6903

Reexamination Request:
No. 90/010,236, Aug. 5, 2008

Reexamination Certificate for:
Patent No.: 6,080,147
Issued: Jun. 27, 2000
Appl. No.: 09/095,630
Filed: Jun. 10, 1998

(51) Int. Cl.
*A61B 17/52* (2006.01)
*A61B 18/18* (2006.01)

(52) U.S. Cl. ............ 606/9; 606/2; 606/10; 606/13
(58) Field of Classification Search .............. None
See application file for complete search history.

(56) References Cited

U.S. PATENT DOCUMENTS 5,626,631 A 5/1997 Eckhouse 5,885,273 A * 3/1999 Eckhouse et al. .............. 606/9

OTHER PUBLICATIONS

Dierickx, C.C. et al., "Thermal Relaxation of Port–Wine Stain Vessels Probed *In Vivo*: The Need for 1–10–Millisecond Laser Pulse Treatment," *J. Invest. Dermatol.* 105:709–714, 1995 ("Dierickx").

* cited by examiner

*Primary Examiner*—Robert M. Fetsuga

(57) ABSTRACT

A method of removing hair or blood vessels from the skin of a patient using a flashlamp, a sequence control device and an optical delivery system, and includes the steps of controlling the flashlamp to sequentially emit a series of pulses of incoherent light energy, transmitting the series of pulses of incoherent light energy through the optical delivery system to the same spot on the skin containing the hair or blood vessels with the sequential pulses of incoherent light energy transmitted through the optical delivery system from the flashlamp, and pulsing the flashlamp at least two times at a wavelength in the range 550 to 1200 nm, at a power level in the range of 4 to 25 Joules/cm$^2$, each pulse having a duration in the range of ½ to 10 milliseconds, a delay between pulses in the range of 1 to 10 milliseconds, and having a beam diameter on the treatment area in the range of 4 to 50 millimeters.

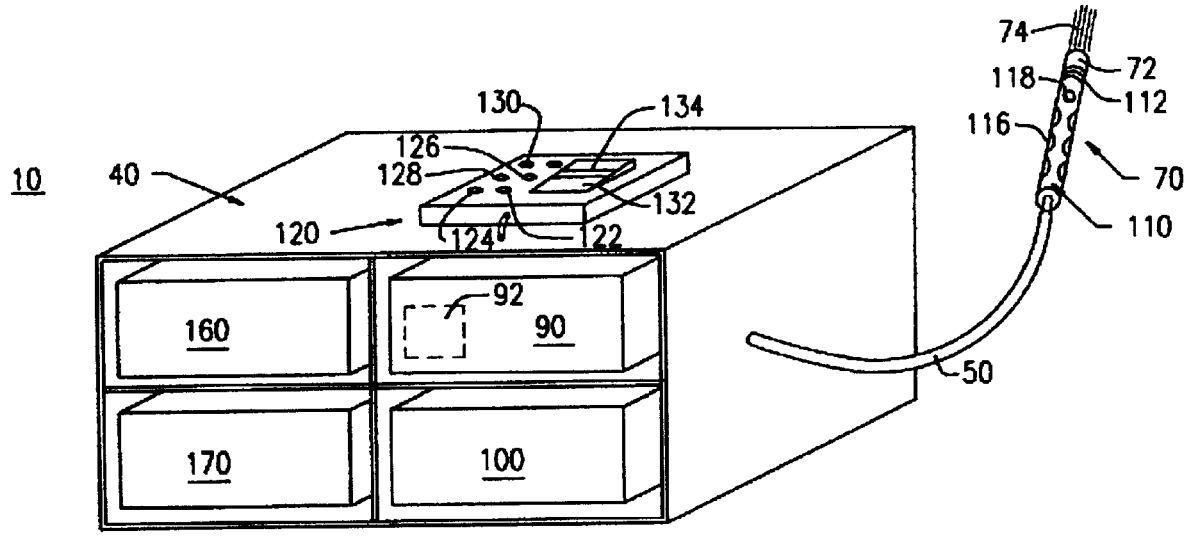

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-8 are cancelled.

* * * * *